United States Patent
Murphy (10) Patent No.: US 11,311,698 B2
(45) Date of Patent: Apr. 26, 2022

(54) FORCE LIMITING HANDLE ASSEMBLY AND HEART CATHETER BASED DELIVERY

(71) Applicant: Creganna Unlimited Company, Galway (IE)

(72) Inventor: Brian Murphy, Galway (IE)

(73) Assignee: Creganna Unlimited Company, Galway (IE)

(*) Notice: Subject to any disclaimer, the term of this patent is extended or adjusted under 35 U.S.C. 154(b) by 270 days.

(21) Appl. No.: 16/413,950

(22) Filed: May 16, 2019

(65) Prior Publication Data

US 2019/0351188 A1    Nov. 21, 2019

(30) Foreign Application Priority Data

May 17, 2018  (EP) ...................................... 18172851

(51) Int. Cl.
| | |
|---|---|
| *A61M 25/01* | (2006.01) |
| *A61F 2/95* | (2013.01) |
| *A61B 90/00* | (2016.01) |

(52) U.S. Cl.
CPC .......... *A61M 25/0136* (2013.01); *A61F 2/95* (2013.01); *A61B 2090/031* (2016.02); *A61F 2/9517* (2020.05); *A61F 2002/9534* (2013.01)

(58) Field of Classification Search
CPC .... A61F 2/2427; A61F 2/2466; A61F 2/9517; A61M 25/0136
See application file for complete search history.

(56) References Cited

U.S. PATENT DOCUMENTS

| | | | | |
|---|---|---|---|---|
| 8,231,569 B2* | 7/2012 | Grasse | ............... | A61M 25/0136 604/95.04 |
| 8,574,241 B2* | 11/2013 | Sjostedt | .................. | A61N 1/056 606/129 |
| 10,064,721 B2* | 9/2018 | Lim | ........................ | A61F 2/2439 |
| 10,279,146 B2* | 5/2019 | Ivinson | ................... | B25B 23/18 |
| 10,292,850 B2* | 5/2019 | Vad | ......................... | A61F 2/9661 |
| 10,441,449 B1* | 10/2019 | Longo | ...................... | A61F 2/966 |
| 10,449,073 B1* | 10/2019 | Longo | ............... | A61M 25/0662 |
| 10,575,951 B2* | 3/2020 | Johnson | ................ | A61F 2/2418 |
| 2007/0088421 A1* | 4/2007 | Loewen | .................... | A61F 2/95 623/1.11 |

(Continued)

FOREIGN PATENT DOCUMENTS

| | | |
|---|---|---|
| EP | 2832318 A1 | 2/2015 |
| WO | 2007139457 A1 | 12/2007 |

OTHER PUBLICATIONS

Extended European Search Report, App. No./Patent No. 18172851.0-1113, dated Nov. 22, 2018, 9 pages.

(Continued)

*Primary Examiner* — Ryan J. Severson
(74) *Attorney, Agent, or Firm* — Barley Snyder (57) ABSTRACT

A handle assembly for a structural heart catheter based delivery system comprises an actuation mechanism connectable to a delivery member and adapted to move the delivery member along a longitudinal axis, a wheel element, and a force limiting coupling unit attaching the wheel element to the actuation mechanism. The force limiting coupling unit disengages the wheel element from the actuation mechanism if a mechanical force applied to the wheel element exceeds a threshold value.

22 Claims, 8 Drawing Sheets

(56) References Cited

U.S. PATENT DOCUMENTS

| | | | |
|---|---|---|---|
| 2007/0168014 A1* | 7/2007 | Jimenez | A61F 2/95 623/1.12 |
| 2009/0248035 A1* | 10/2009 | Sjostedt | A61M 25/0152 606/129 |
| 2012/0150106 A1 | 6/2012 | Grasse et al. | |
| 2012/0330401 A1* | 12/2012 | Sugimoto | A61F 2/915 623/1.12 |
| 2013/0345801 A1 | 12/2013 | Conklin et al. | |
| 2016/0158010 A1* | 6/2016 | Lim | A61F 2/2439 623/1.11 |
| 2019/0351188 A1* | 11/2019 | Murphy | A61F 2/2427 |

OTHER PUBLICATIONS

Communication/Office Action in EP 18172851.0-1113, dated Oct. 15, 2021, 6 pp.

* cited by examiner

FORCE LIMITING HANDLE ASSEMBLY AND HEART CATHETER BASED DELIVERY

CROSS-REFERENCE TO RELATED APPLICATION

This application claims the benefit of the filing date under 35 U.S.C. § 119(a)-(d) of European Patent Application No. 18172851.0, filed on May 17, 2018.

FIELD OF THE INVENTION

The present invention relates to a handle assembly and, more particularly, to a handle assembly for a structural heart catheter based delivery system.

BACKGROUND

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication.

An example of an intravascular procedure that significantly reduces procedure and recovery time and cost over conventional open surgery is a heart valve replacement or repair procedure, in which an artificial valve or valve repair device is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

It is known to use an actuating wheel element that is manually actuated to perform a longitudinal movement of, for instance, a deployment mechanism. However, the problem may occur that a too high mechanical force is applied to the wheel element, so that the handle assembly and/or the delivery system is damaged. This is fatal for the surgery to be performed. There is a need for a handle assembly that has a higher degree of safety during use, at the same time being robust and economic to manufacture.

SUMMARY

A handle assembly for a structural heart catheter based delivery system comprises an actuation mechanism connectable to a delivery member and adapted to move the delivery member along a longitudinal axis, a wheel element, and a force limiting coupling unit attaching the wheel element to the actuation mechanism. The force limiting coupling unit disengages the wheel element from the actuation mechanism if a mechanical force applied to the wheel element exceeds a threshold value.

BRIEF DESCRIPTION OF THE DRAWINGS

The invention will now be described by way of example with reference to the accompanying Figures, of which.

DETAILED DESCRIPTION OF THE EMBODIMENT(S)

The accompanying drawings are incorporated into the specification and form a part of the specification to illustrate several embodiments of the present invention. These drawings, together with the description serve to explain the principles of the invention. The drawings are merely for the purpose of illustrating how the invention can be made and used, and are not to be construed as limiting the invention to only the illustrated and described embodiments. Furthermore, several aspects of the embodiments may form—individually or in different combinations—solutions according to the present invention. The following described embodiments thus can be considered either alone or in an arbitrary combination thereof. Further features and advantages will become apparent from the following more particular description of the various embodiments of the invention, as illustrated in the accompanying drawings, in which like references refer to like elements.

Figure 1:
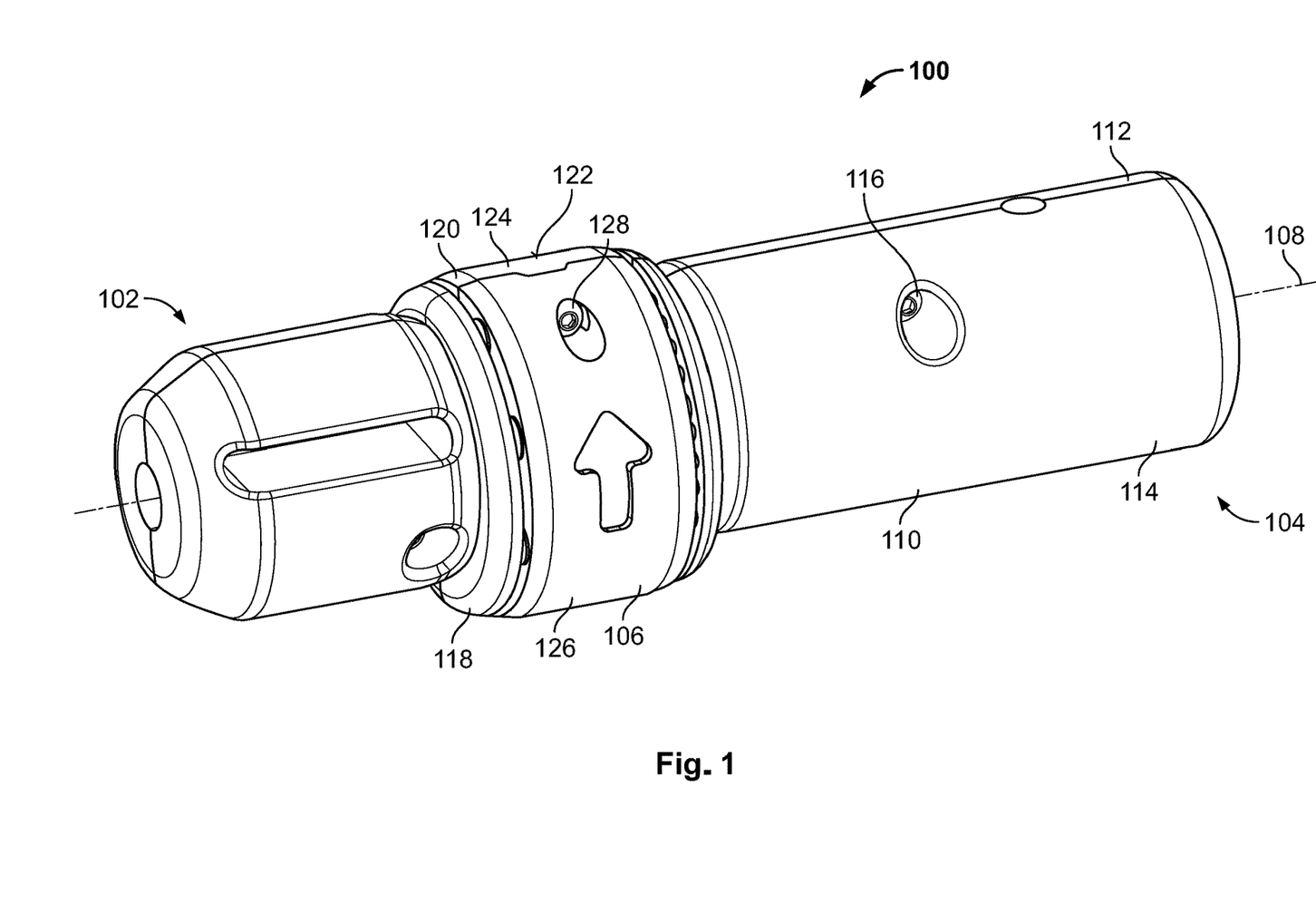
FIG. 1 is a perspective view of a handle assembly according to an embodiment.
Figure 2:
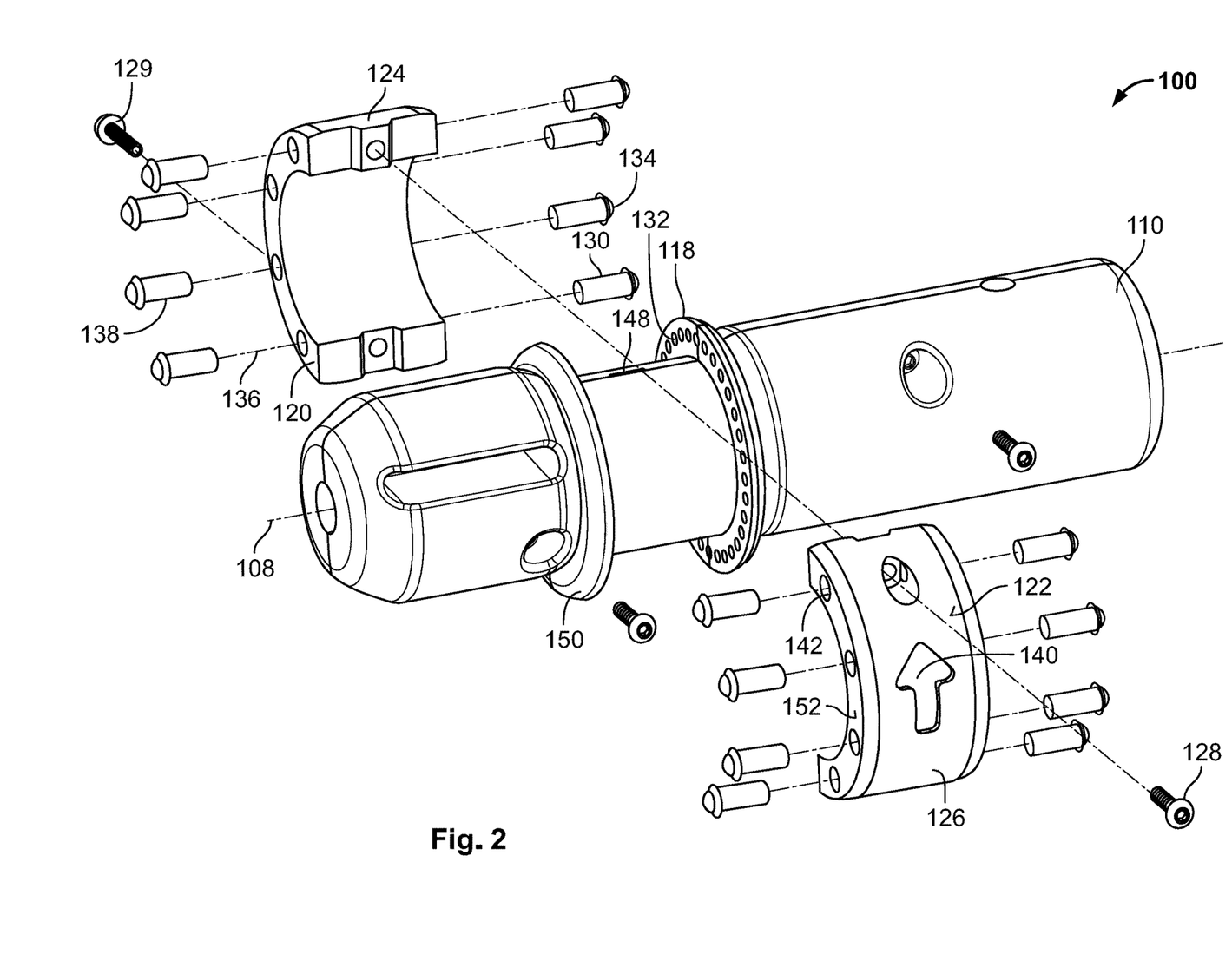
FIG. 2 is an exploded perspective view of the handle assembly.

A handle assembly 100 according to an embodiment is shown in FIGS. 1 and 2. The handle assembly has a distal end 102 and a proximal end 104. As used herein, the terms "proximal" and "distal" are to be taken as relative to a user using the disclosed delivery devices. "Proximal" is to be understood as relatively close to the user and "distal" is to be understood as relatively farther away from the user.

Figure 7:
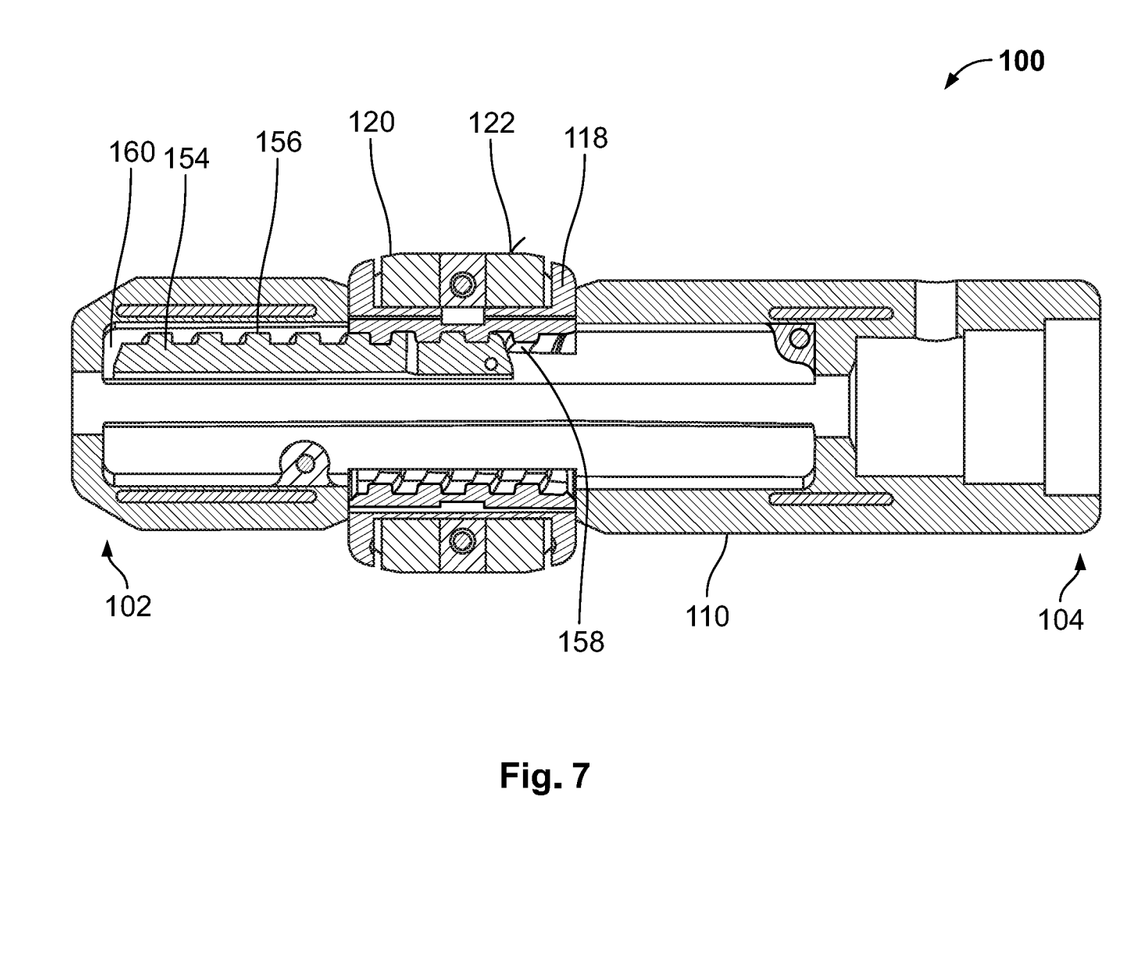
FIG. 7 is a sectional side view of the handle assembly.
Figure 8:
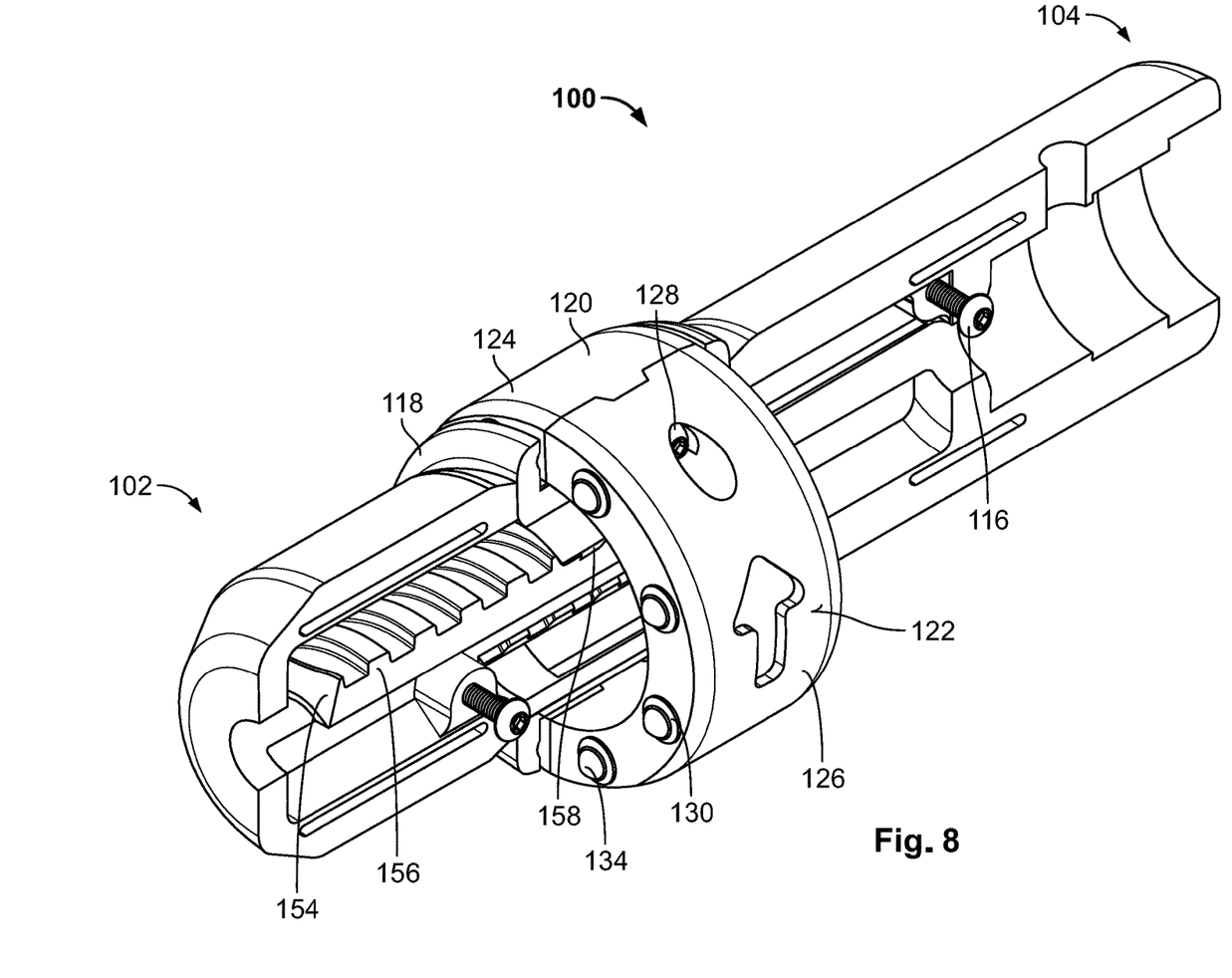
FIG. 8 is a partially sectional perspective view of the handle assembly.
Figure 9:
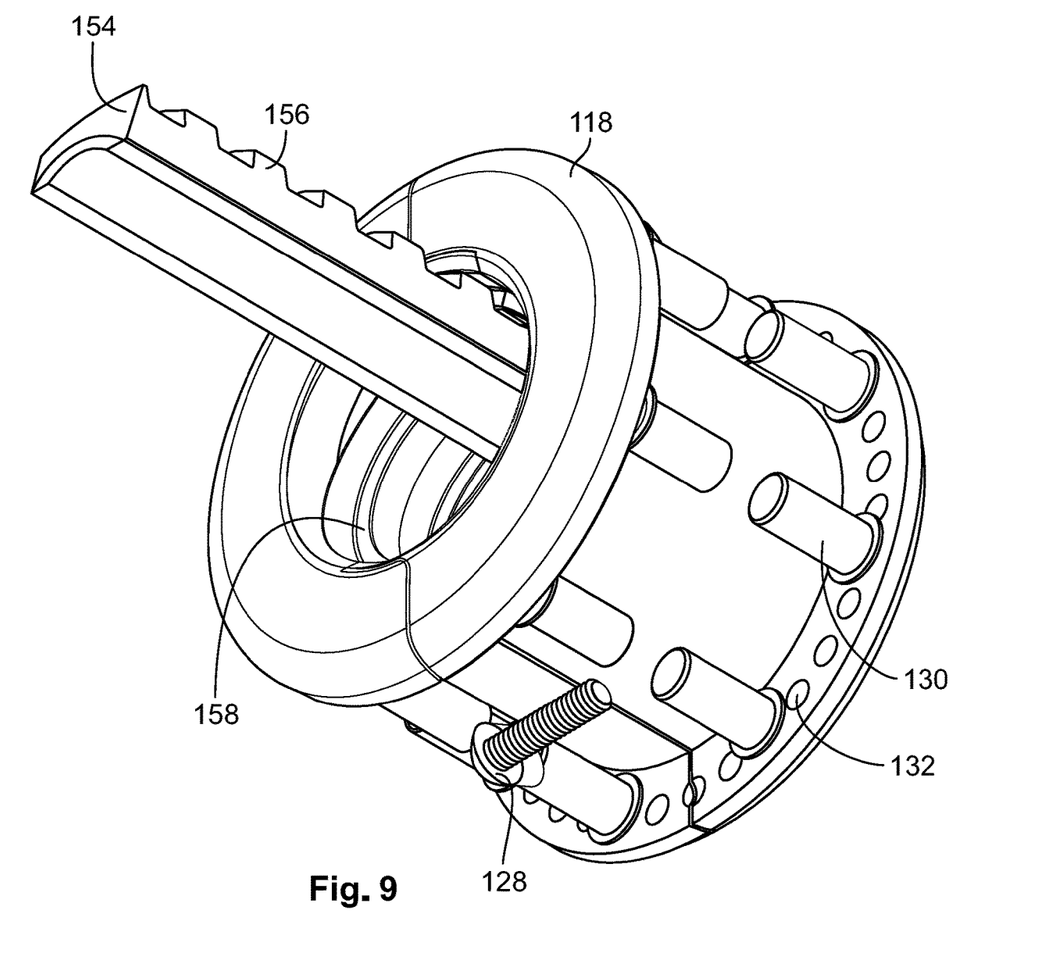
FIG. 9 is a perspective view of an inner bearing element and an actuating rod of the handle assembly.

The handle assembly 100 comprises an actuation mechanism, shown in the FIGS. 7-9, that allows a translation of a rotational movement of a wheel element 106 around a longitudinal axis 108 into a linear movement along the longitudinal axis 108. In another embodiment, the wheel element 106 can rotate around an axis transverse to the longitudinal axis 108 and translate into a linear movement along the longitudinal axis 108.

The handle assembly 100, as shown in FIGS. 1 and 2, comprises a housing 110 which is formed by a first and a second half-shell 112, 114. The first half-shell 112 and the second half-shell 114 are connected to each other by a first screw connection 116. The housing 110 may be fabricated from a plastic material, and may be fabricated by injection molding.

The wheel element 106, as shown in FIGS. 1 and 2, has an inner bearing element 118, which is inwardly connected to the actuation mechanism. The inner bearing element 118 is coupled to an outer bearing element 120 which has an actuation surface 122 that can be touched by a user in order to rotate the wheel element 106. The inner bearing element 118 and the outer bearing element 120 form a force limiting coupling unit attaching the wheel element 106 to the actuation mechanism. In an embodiment, the actuation surface 122 may have a suitable surface finish that improves a grip of the user. In an embodiment, the inner bearing element 118 is arranged concentrically with the outer bearing element 120 around the rotational axis.

As shown in FIG. 2, the outer bearing element 120 is fabricated from two separately fabricated segments 124, 126 which are connected to each other by a second screw connection 128. The segments 124, 126 are joined along interfaces that extend along the longitudinal axis 108. The outer bearing element 120 has a tube shape with a pair of end faces 152.

As shown in FIG. 2, the inner bearing element 118 is coupled to the outer bearing element 120 via spring-loaded ball plungers 130. The inner bearing element 118 has a plurality of recesses 132 into which balls 134 of the spring-loaded ball plungers 130 engage. The balls 134 and recesses 132 are distributed equidistantly around a circumference of the end faces 152 and the inner bearing element 118. The individual ball plungers 130 are held inside cavities 142 that are provided at the outer bearing element 120. In the shown embodiment, each of the cavities 142 is formed by a blind hole, which facilitates mounting the ball plungers 130. In another embodiment, through holes which extend along the complete length of the outer bearing element 120 along the longitudinal axis 108 can be provided as the cavities 142. In another embodiment, the balls 134 can also be arranged on the inner bearing 118, while the recesses 132 are arranged on the rotatable outer bearing 120. The balls 134 protrude beyond at least one of the end faces 152.

Figure 3:
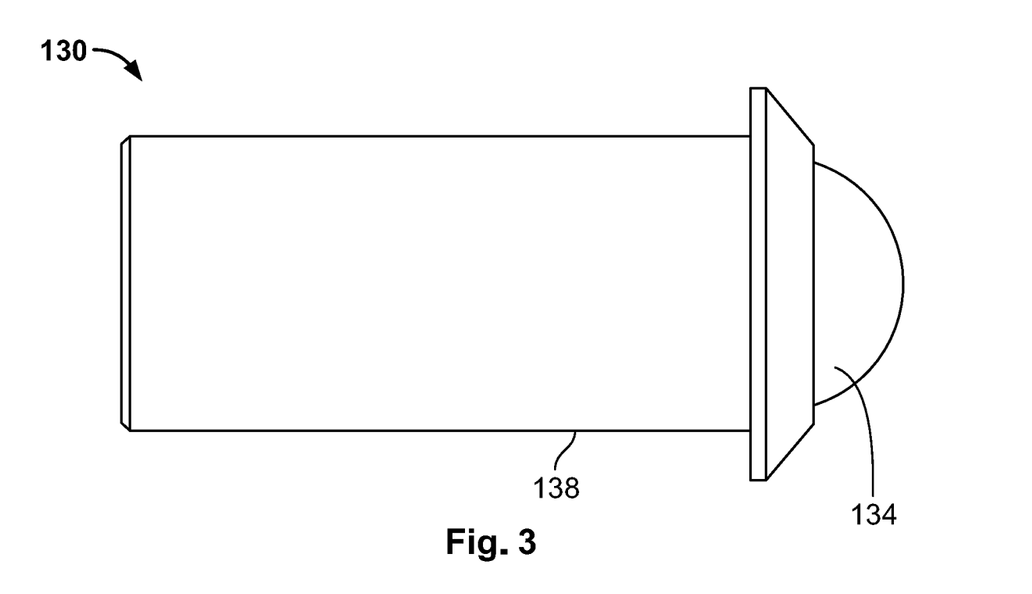
FIG. 3 is a side view of a ball plunger of the handle assembly.
Figure 4:
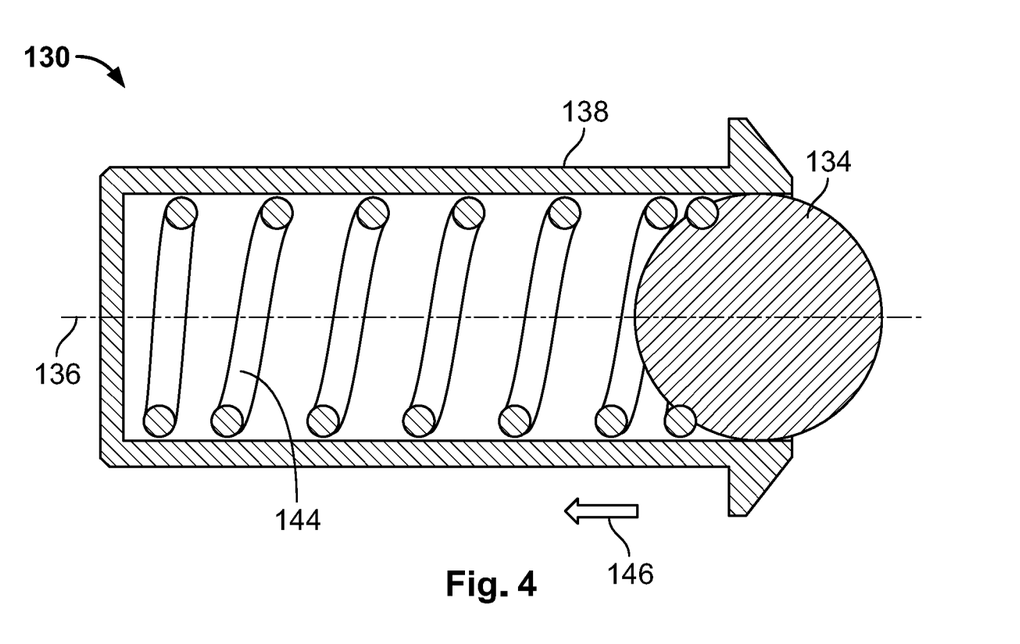
FIG. 4 is a sectional side view of the ball plunger.

As shown in FIGS. 3 and 4, the balls 134 are spring-loaded along their respective longitudinal axes 136, so that they each can be pressed into the bodies 138 of the ball plungers 130. Consequently, when the user turns the wheel element 106 by rotating the actuation surface 122 in a rotary direction as indicated by the arrow 140, the outer bearing element 120 and the inner bearing element 118 will stay connected to each other as long as a certain threshold value of the applied torque is not exceeded. Under these conditions, with the inner and the outer bearing elements 118, 120 being coupled, the actuation mechanism inside the handle assembly 100 is actuated by the rotary motion caused by the user.

However, as soon as a particular threshold value of a maximum admissible torque is exceeded, the forces that are exerted on the balls 134 become sufficiently high that each ball 134 is pressed into the body 138 of the ball plunger 130, so that the outer bearing element 120 rotationally slips with respect to the inner bearing element 118. The internal actuation mechanism is then no longer actuated by the rotary motion performed by the user, thereby effectively avoiding damaging the actuation mechanism and the components associated therewith. The user advantageously hears and/or senses this slipping between the inner bearing element 118 and the outer bearing element 120 and may reduce the exerted rotational force. By the slipping motion, the balls 134 each exit from the respective recess 132 and glide into a radially adjacent one. Thereby, the inner bearing element 118 and the outer bearing element 120 are coupled with each other again and the internal actuation mechanism may be actuated again by the user rotating the actuation surface 122.

The value of the maximum torque, until which the inner bearing element 118 and the outer bearing element 120 stay mechanically coupled, is determined by the spring constants of the ball plungers 130 and by the total amount of ball plungers 130 used for the coupling. In the embodiment shown in FIG. 2, sixteen ball plungers 130 are used. Moreover, as can be seen in FIG. 2, the number of recesses 132 provided at the inner bearing element 118 is higher. Consequently, by using a different outer bearing element 120 with more ball plungers 130 integrated therein, a higher admissible torque may be achieved. However, in other embodiments, the number of recesses 132 which are distributed evenly around the circumference of the inner bearing element 118 may of course also exactly correspond to the number of ball plungers 130.

The balls 134 may of course also be assembled directly inside the cavities 142, using springs and balls as separate parts, which are inserted into the cavities 142. However, the fabrication of the handle assembly 100 is significantly facilitated by using prefabricated ball plungers 130.

The outer bearing element 120, as shown in FIGS. 1 and 2, is formed by a first segment 124 and a second segment 126. The two segments 124, 126 are attached to each other by second screw connections 128, 129. In other embodiments, however, more than two segments may also be provided. Segmented fabrication facilitates an injection molding process. Furthermore, as shown in FIG. 2, the two half-shells 124, 126 each having a C-shaped cross-section may be formed by two identical parts which are interconnected asymmetrically. In other embodiments, the segments 124, 126 can be connected by a snap-lock device, by a glue, or by a laser welding. In another embodiment, at least one of the longitudinal interfaces between the segments 124, 126 can be formed by a film hinge, a thin section of plastic that flexibly connected the segments 124, 126. The film hinge may be formed from a polypropylene or a polyethylene.

Each of the ball plungers 130 has the body 138 which may, for instance, be made from metal, such as stainless steel. The ball 134 is assembled inside the body 138 and supported by a spring 144, as shown in FIG. 4. The diameter of the opening is smaller than the inside diameter of the body 138, so that the ball 134 cannot escape. If a sufficiently high force component is exerted along the axis 136, the ball 134 may be pushed inside the body 138 as indicated by the arrow 146. The force that is necessary for pressing the ball 134 in the direction 146 is determined by the spring characteristics of the spring 144. The total amount of balls 134 used for coupling the inner coupling 118 with the outer coupling 120 determines the maximum torque that is allowable before the mechanical coupling between the inner bearing 118 and the outer bearing 120 discontinues.

Figure 5:
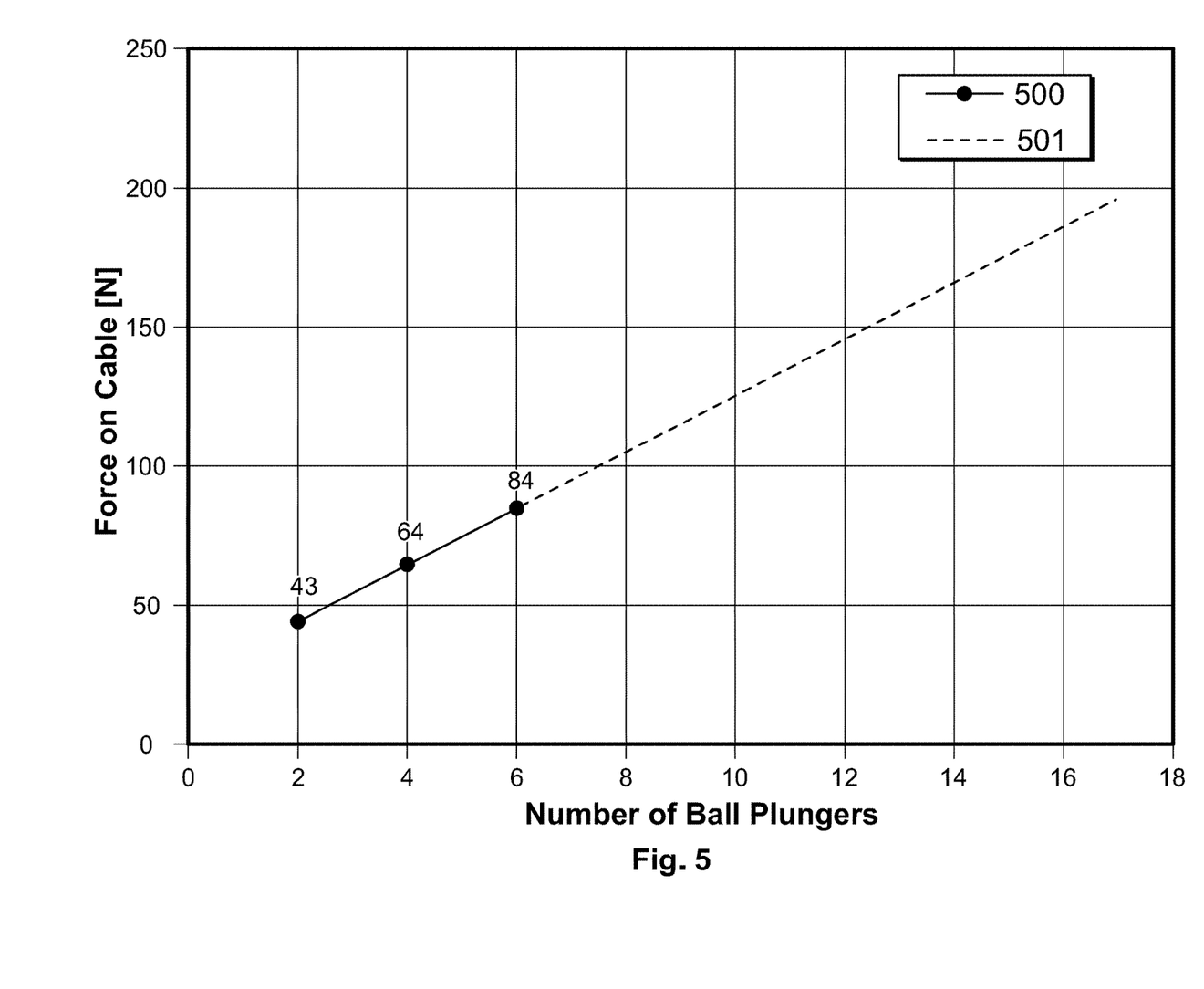
FIG. 5 is a chart of a relationship between a force threshold value and a number of ball plungers used in the handle assembly.
Figure 6:
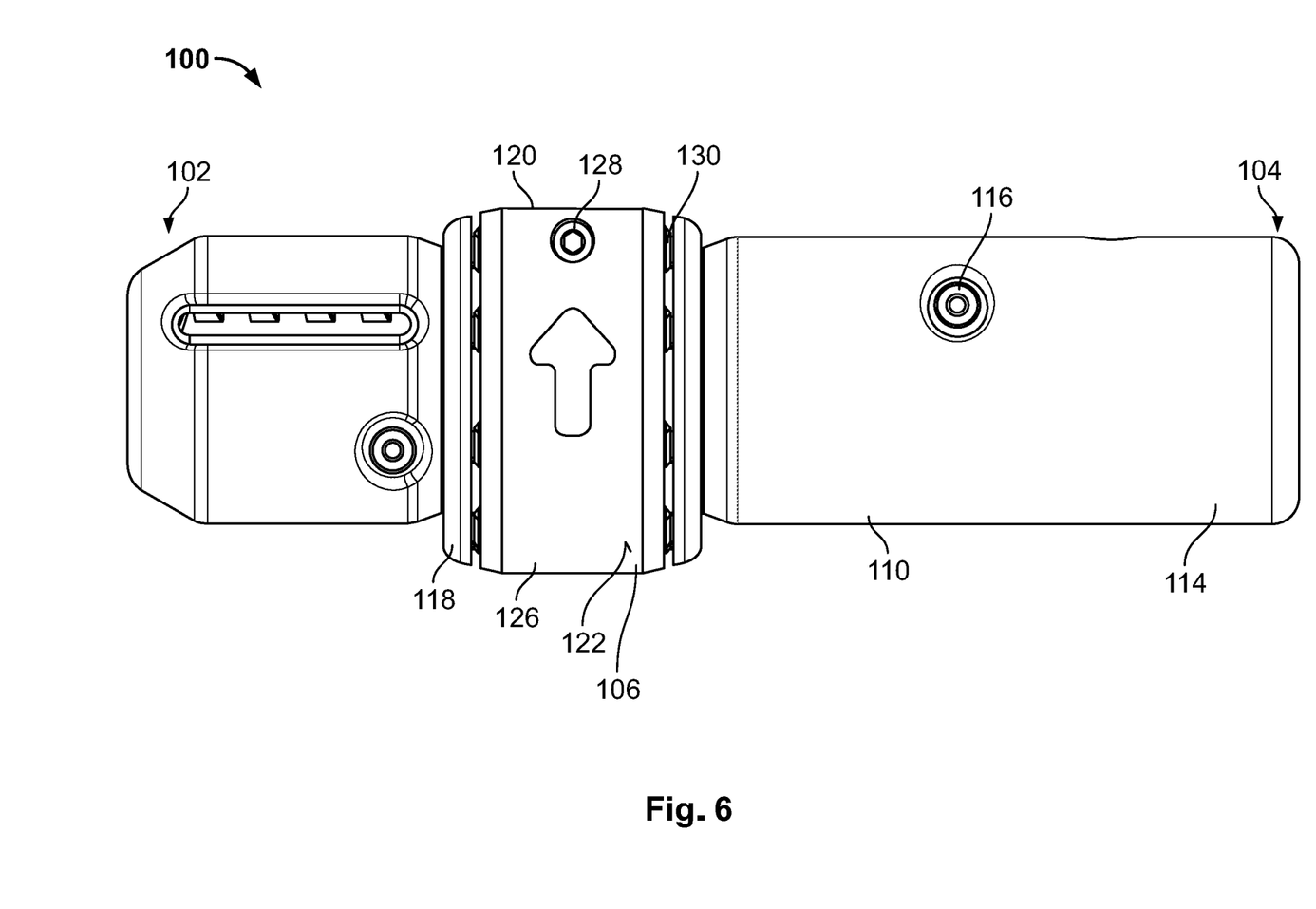
FIG. 6 is a side view of the handle assembly.

A maximum force in N which can be exerted, for instance, on a deployment cable of a delivery device depending on the amount of ball plungers 130 used is shown in FIG. 5. The graph shows a linear correlation between the number of ball plungers 130 and the force inside the handle. Consequently, with just a few measured results, the number of plungers 130 needed for a particular handle design can be extrapolated.

Curve 500 indicates the actually performed measurements, while the broken line 501 is a linear extrapolation on the expected force values for higher numbers of ball plungers 130. As shown in FIG. 5, using two ball plungers 130 allows a coupling between the inner bearing element 118 and the outer bearing element 120 up to a force of 43 N. Using four ball plungers 130 keeps the connection established until a threshold value of 64 N is reached. Finally, with six ball plungers 130, a maximum torque of 84 Newton can be reached before the coupling is disengaged. It is to be expected that this linear dependence will at least be valid also for a number of sixteen ball plungers as shown in FIG. 2, so that a threshold value of below 200 N will be reached with this arrangement.

The assembly of a handle according to an embodiment will now be described in detail with reference to FIGS. 1-4.

First, the actuation mechanism that translates a rotational motion into a linear motion is mounted inside the housing 110 of the handle assembly 100. The actuation mechanism is connectable to a delivery member and adapted to move the delivery member in the longitudinal direction 108. Next the inner bearing 118 is mounted at the housing 110 so that it is rotatable with respect to the housing 110. The inner bearing 118 may be fabricated from two half-shells which are connected to each other by a snap fit connection 148. The tube shaped inner bearing element 118 has a circumferential collar 150 at a peripheral end that has recesses 132 at its inside for engaging with the balls 134.

In a next step, the first half-shells 124 and the second half-shells 126 of the outer bearing element 120, which are provided with cavities 142 at the end faces 152 of the outer bearing element 120, are equipped with a plurality of ball plungers 130. The first half-shell 124 and the second half-shell 126 are attached to the inner bearing element 118 and connected with each other to form a cylindrical tube by mounting the screws 128, 129. In this stage, the balls 134 each engage with one recess 132 while some recesses 132 at the inner bearing element 118 stay empty. The inner bearing element 118 may be referred to as a first bearing element and the outer bearing element 120 may be referred to as a second bearing element.

The actuation mechanism that translates the rotatory movement of the wheel element 106 into a translatory movement will now be described in more detail with reference to FIGS. 6-9.

In an embodiment, the actuation mechanism is based on a screw drive mechanism. As shown in FIG. 7, the handle assembly 100 includes an actuating rod 154 which has a screw thread 156 arranged on its outer surface. The wheel element 106 is formed to be operated as the nut of the screw drive. In particular, the inner bearing 118 of the wheel element 106 has an essentially cylindrical shape and is provided on its inner surface with a nut thread 158. The nut thread 158 is engaged with the screw thread 156, so that a rotating movement of the wheel element 106 is transformed into an axial movement of the actuating rod 154 along the axis 108.

The actuating rod 154, as shown in FIGS. 7-9, is arranged in a guiding recess 160 within the housing 110 of the handle assembly 100. The actuating rod 154 may be connected to a sheath, which covers a component to be delivered. That is, when the wheel element 106 is in threaded engagement with the threaded actuating rod 154, rotation of the wheel element 106 in one direction (either clockwise or counterclockwise depending on the orientation of the threads on the threaded actuating rod 154) causes the threaded actuating rod 154 to move proximally within the guiding recess 160, at the same time pulling the sheath in a distal direction to uncover an expandable component. The user rotating the actuation surface 122 can only apply an actuating force until the maximum torque has been reached and the ball plungers 130 disengage from the recesses 132. If the maximum torque has been reached, the actuation surface 122 is decoupled from the actuating rod 154.

The present invention further relates to a structural heart catheter based delivery system for intravascularly delivering replacement components, the delivery system comprising a catheter assembly and the handle assembly 100. In an embodiment, the delivery system can be used with prosthetic heart valve replacement, and can be used with devices, systems, and methods for transapical and transcatheter delivery of collapsible prosthetic heart valves. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size. When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size.

For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn. In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically re-sheathes the annulus end of the valve, so that the valve can be repositioned while in a collapsed state. After the valve has been repositioned, the user can again release the valve.

All these movements in a longitudinal direction are translated into a rotational motion by actuation of the handle assembly 100. In order to ensure a maximum level of sterility with lowest possible sterilization efforts, the handle assembly 100 is disposable and can be replaced by a completely new unit for the next surgery.

The handle assembly 100 avoids breaking a delivery device by applying a too high torque force because the torque limiting bearing between the inner bearing element 118 and the outer bearing element 120 prevents the device from reaching the breaking point. The level of permissible force is limited to a chosen threshold value. Moreover, by using a coupling between the ball 134 and the recess 132, the design produces similar results in wet and dry conditions.

Because the handle assembly 100 can easily be disassembled to add or remove one or more ball plungers 130, the handle assembly 100 may further be used for testing new delivery systems. In particular, the present invention relates to a method of testing one or more component(s) of a structural heart catheter based delivery system. In a heart valve delivery system where the occurring forces are not yet known, where new approaches are investigated, and where new untested valve designs are used, the handle assembly 100 according to the present invention as shown in FIGS. 1-4 and 6-9 can be used to estimate the forces in the delivery system.

Because the handle 100 is serviceable in the field with only two screws, one can quickly add and subtract ball plungers 130. For instance, the testing routine may start with one pair of ball plungers 130 and the handle 100 is actuated for testing the force. If the handle slips, another ball plunger 130 is added and the testing is repeated until the force needed for actuation is reached. Then the number of ball plungers 130 that are required is counted. A look-up table or chart based on the correlation shown in FIG. 5 may be provided to indicate the force value corresponding to the number of ball plungers 130 which are minimally needed for actuating the actuating unit. This force value will be +/− one ball plunger worth of actual force.

As mentioned above, the testing method according to the present invention comprises the following steps:

(a) providing a handle assembly 100 with a first number of ball plungers 130;

(b) delivering force to the wheel element 106 and determining whether the threshold value of the permissible force has been reached;

(c) if the threshold value has been reached and the wheel element 106 has disengaged from the actuation unit, adding at least one further ball plunger 130, and repeating step (b), or (d) if the threshold value is no longer reached and the wheel element 106 stays engaged with the actuation unit, counting the number of ball plungers 130 contained in the handle assembly 100, and (e) determining the force necessary to actuate the delivery system from the smallest number of ball plungers 130 sufficient to keep the wheel element 106 engaged with the actuation unit.

According to this method, no additional and costly measurement devices are needed and the method can therefore easily be performed in the field.

What is claimed is:

1. A handle assembly for a structural heart catheter based delivery system, comprising:
   an actuation mechanism connectable to a delivery member and adapted to move the delivery member along a longitudinal axis;
   a wheel element; and
   a force limiting coupling unit attaching the wheel element to the actuation mechanism, the force limiting coupling unit disengaging the wheel element from the actuation mechanism if a mechanical force applied to the wheel element exceeds a threshold value, the force limiting coupling unit has a ball that engages a recess as long as the mechanical force does not exceed the threshold value.

2. The handle assembly of claim 1, wherein the force limiting coupling unit has a ball plunger, the ball plunger having a body and the ball spring-loaded in the body.

3. The handle assembly of claim 1, wherein the wheel element is rotatable around the longitudinal axis.

4. The handle assembly of claim 3, wherein the force limiting coupling unit has an inner bearing element coupled to the actuation mechanism and an outer bearing element accessible by a user.

5. The handle assembly of claim 4, wherein the outer bearing element is engaged with the inner bearing element as long as the mechanical force is below the threshold value.

6. The handle assembly of claim 5, wherein the outer bearing element has a pair of segments that are interconnected with each other along an interface that extends along the longitudinal axis.

7. The handle assembly of claim 5, wherein the outer bearing element has a tube shape with a pair of end faces and a plurality of balls spring-loaded along the longitudinal axis.

8. The handle assembly of claim 7, wherein the balls protrude beyond at least one of the end faces.

9. The handle assembly of claim 8, wherein the inner bearing element has a tube shape with a collar arranged at a peripheral end of the tube around a circumference of the tube.

10. The handle assembly of claim 9, wherein the collar has a plurality of recesses engaging the balls.

11. The handle assembly of claim 10, wherein the balls and the recesses are distributed equidistantly around a circumference of the at least one end face and the collar.

12. The handle assembly of claim 11, wherein each of the balls disengages from a recess when the mechanical force exceeds the threshold value and engages with an adjacent recess.

13. The handle assembly of claim 4, wherein the outer bearing element has a plurality of ball plungers arranged along the longitudinal axis.

14. A delivery system for intravascularly delivering replacement components, comprising:
   a handle assembly including an actuation mechanism connectable to a delivery member and adapted to move the delivery member along a longitudinal axis, a wheel element, and a force limiting coupling unit attaching the wheel element to the actuation mechanism, the force limiting coupling unit disengaging the wheel element from the actuation mechanism if a mechanical force applied to the wheel element exceeds a threshold value, the force limiting coupling unit has a ball that engages a recess as long as the mechanical force does not exceed the threshold value.

15. A handle assembly for a structural heart catheter based delivery system, comprising:
   an actuation mechanism connectable to a delivery member and adapted to move the delivery member along a longitudinal axis;
   a wheel element rotatable around the longitudinal axis; and
   a force limiting coupling unit attaching the wheel element to the actuation mechanism, the force limiting coupling unit disengaging the wheel element from the actuation mechanism if a mechanical force applied to the wheel element exceeds a threshold value, the force limiting coupling unit has an inner bearing element coupled to the actuation mechanism and an outer bearing element accessible by a user, the outer bearing element is engaged with the inner bearing element as long as the mechanical force is below the threshold value.

16. The handle assembly of claim 15, wherein the outer bearing element has a pair of segments that are interconnected with each other along an interface that extends along the longitudinal axis.

17. The handle assembly of claim 15, wherein the outer bearing element has a tube shape with a pair of end faces and a plurality of balls spring-loaded along the longitudinal axis.

18. The handle assembly of claim 17, wherein the balls protrude beyond at least one of the end faces.

19. The handle assembly of claim 18, wherein the inner bearing element has a tube shape with a collar arranged at a peripheral end of the tube around a circumference of the tube.

20. The handle assembly of claim 19, wherein the collar has a plurality of recesses engaging the balls.

21. The handle assembly of claim 20, wherein the balls and the recesses are distributed equidistantly around a circumference of the at least one end face and the collar.

22. The handle assembly of claim 21, wherein each of the balls disengages from a recess when the mechanical force exceeds the threshold value and engages with an adjacent recess.

\* \* \* \* \*